United States Patent
Roig et al.

(10) Patent No.: US 9,594,024 B2
(45) Date of Patent: Mar. 14, 2017

(54) METHOD FOR CORRECTING A SIGNAL BACKSCATTERED BY A SAMPLE AND ASSOCIATED DEVICE

(71) Applicant: Commissariat a L'Energie Atomique et aux Energies Alternatives, Paris (FR)

(72) Inventors: Blandine Roig, Guemene sur Scorff (FR); Anne Koenig, Saint Martin d'Uriage (FR); Jean-Marc Dinten, Lyons (FR); Francois Perraut, Saint Joseph de Riviere (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 0 days.

(21) Appl. No.: 15/015,325

(22) Filed: Feb. 4, 2016

(65) Prior Publication Data
US 2016/0231249 A1    Aug. 11, 2016

(30) Foreign Application Priority Data
Feb. 6, 2015   (FR) ...................................... 15 50983

(51) Int. Cl.
*G01J 3/44* (2006.01)
*G01N 21/65* (2006.01)
(Continued)

(52) U.S. Cl.
CPC ............. *G01N 21/65* (2013.01); *G01N 21/49* (2013.01); *G01N 21/6458* (2013.01);
(Continued)

(58) Field of Classification Search
CPC ... G01J 3/44; G01J 3/02; G01N 21/65; G01N 21/658
See application file for complete search history.

(56) References Cited

U.S. PATENT DOCUMENTS

| | | | | |
|---|---|---|---|---|
| 5,828,450 A | * | 10/1998 | Dou ...................... | G01J 3/4412 250/339.07 |
| 2007/0057211 A1 | * | 3/2007 | Bahlman ............ | G01N 21/6452 250/584 |

(Continued)

OTHER PUBLICATIONS

French Preliminary Search Report issued Dec. 21, 2015 in French Application 15 50983, filed Feb. 6, 2015 (with English Translation of Categories of Cited Documents and Written Opinion).

(Continued)

*Primary Examiner* — Abdullahi Nur
(74) *Attorney, Agent, or Firm* — Oblon, McClelland, Maier & Neustadt, L.L.P.

(57) ABSTRACT

The invention relates to a method for correcting an optical signal produced by a sample comprising the following steps:
  illuminating a surface of the sample by a first light beam, produced by a first light source, the said first light source being coupled to a first optical system, focusing the said first light beam in an object focal plane of the first optical system, the said object focal plane being situated, in the sample, at a measuring depth z from the surface of the sample;
  measuring, with a first photodetector, of a first optical signal backscattered by the sample in response to the first light beam, the first photodetector producing a first measured signal representative of the said first optical signal, a spatial filter being interposed between the first optical system and the first photodetector, the spatial filter comprising a window which transmits the said first optical signal towards the said first photodetector, the window being disposed in a conjugate focal plane of the object focal plane of the first optical system;
wherein the method also comprises the following steps:
  determining an optical scattering property of the sample;
(Continued)

applying a correction function to the first measured signal so as to generate a first corrected signal, the said correction function taking into account the said optical scattering property.

23 Claims, 10 Drawing Sheets

(51) Int. Cl.
G01N 21/64 (2006.01)
G01N 21/49 (2006.01)
G01N 21/27 (2006.01)
G02B 21/00 (2006.01)

(52) U.S. Cl.
CPC ............ *G01N 21/6486* (2013.01); *G01J 3/44* (2013.01); *G01N 21/274* (2013.01); *G01N 2201/06113* (2013.01); *G01N 2201/0833* (2013.01); *G01N 2201/121* (2013.01); *G02B 21/0076* (2013.01)

(56) References Cited

U.S. PATENT DOCUMENTS

2011/0301438 A1 12/2011 Sachse et al.
2014/0241994 A1 8/2014 Koenig

OTHER PUBLICATIONS

B. Roig et al. "Correction of Deep Raman Spectra Distorted by Elastic Scattering", Microtechnologies for Biology and Healthcare, Annual Research Report, 2014, 3 pages.

Jing Yang et al. "Quantitative Raman Spectrometry: The Accurate Determination of Analytes in Solution Phase of Turbid Media", Chemometrics and Intelligent Laboratory Systems, vol. 126, 2013, 5 pages.

Anne Koenig et al. "Diffuse Reflectance Spectroscopy: A Clinical Study of Tuberculin Skin Tests Reading" Proc. of SPIE, vol. 8592, 2013, 8 pages.

"Confocal Microscopy" Wikipedia, Feb. 5, 2015 URL: https•//en.wikipedia.org/w/index.php?title=Special:Book&bookcmd=download&collection_id=d09ad73107leaf1d844acec4a3af9022b95c18dc&writer=rdf2latex&return_to=Confocalmicroscopy, 6 pages.

Steven L. Jacques et al. "Reflectance Confocal Microscopy of Optical Phantoms", Biomedical Optics Express, vol. 3, No. 6, 2012, 11 pages.

A. M. MacDonald et al. "On Confocal Raman Spectroscopy of Semicrystalline Polymers: The Effect of Optical Scattering", Applied Spectroscopy, vol. 57, No. 12, 2003, 7 pages.

N. A. Freebody et al. "On Optical Depth Profiling Using Confocal Raman Spectroscopy", Anal Bioanal Chem, vol. 396, 2010, 11 pages.

* cited by examiner

METHOD FOR CORRECTING A SIGNAL BACKSCATTERED BY A SAMPLE AND ASSOCIATED DEVICE

TECHNICAL FIELD

The invention lies in the field of the characterization of samples, and especially biological samples, and more particularly the skin.

DESCRIPTION OF THE PRIOR ART

Optical measurements making it possible to characterize samples are widespread. This entails, in particular, characterizing the optical properties or the nature of the materials of which a sample is composed. Measurements based on the detection of a signal backscattered by a sample illuminated by a light beam may be cited in particular. These entail, in particular, Raman spectrometry, fluorescence imaging or diffuse reflectance spectrometry.

Raman spectroscopy forms part of the customarily used procedures. It is based on the inelastic scattering of photons in a medium, subsequent to the illumination of the medium by a monochromatic light beam. The photons resulting from these inelastic interactions are detected and then processed by a spectroscopy device, making it possible to form a Raman spectrum. Such a spectrum generally comprises a plurality of peaks centred on wave numbers, the latter constituting a signature of the chemical species present in a sample.

Applied to the skin, and in a confocal configuration, Raman spectrometry may in particular be suitable for classification between a healthy tissue and a diseased tissue, or for tracking the migration of a product within the various layers constituting the skin.

However, the skin is a scattering medium and, beyond a certain depth, the Raman spectra are strongly degraded by the disturbances related to the scattering of the light in the sample, whether involving the light of the excitation beam, or the light re-emitted on completion of the inelastic scattering.

Another optical procedure allowing the characterization of a sample is the measurement of fluorescence, whether it be endogenous or exogenous fluorescence. The principle is to illuminate a sample, generally with the aid of a beam whose spectral width is narrow and centred on an excitation wavelength of a fluorophore, and then to measure the fluorescence signal emitted by the fluorophore in response to the illumination beam. The objective is then to locate the position of the fluorophores in the medium.

In this case also, the measurements may be disturbed by the scattering of the light in the medium, whether it be the incident excitation light or the fluorescence light, re-emitted subsequent to the excitation of the fluorophore.

The invention proposes to respond to these drawbacks, and to improve the quality of optical signals emitted by a scattering sample in response to an illumination.

DESCRIPTION OF THE INVENTION

An object of the invention is a method for correction of an optical signal produced by a sample comprising the following steps:
illuminating a surface of the sample by a first light beam, produced by a first light source, the said first light source being coupled to a first optical system, focusing the said first light beam in an object focal plane of the first optical system, the said object focal plane being situated, in the sample, at a measuring depth z below the surface of the sample;
measuring, with a first photodetector, of a first optical signal backscattered by the sample in response to the first light beam, the first photodetector producing a first measured signal representative of the said first optical signal, a spatial filter being interposed between the first optical system and the first photodetector, the spatial filter comprising a window which transmits the said first optical signal towards the said first photodetector, the window being disposed in a conjugate focal plane of the object focal plane of the first optical system;
wherein the method also comprises the following steps:
determining an optical scattering property of the sample;
applying a correction function to the first measured signal so as to generate a first corrected signal, the said correction function taking into account the said optical scattering property.

According to an embodiment, the said optical scattering property is determined at a wavelength of the first light beam. It may be determined at this wavelength alone.

According to an embodiment, the method may comprise determining the said measuring depth between the first object focal plane of the first optical system and the surface of the sample, the correction function taking the measuring depth into account.

According to an embodiment, the first light source is a laser source, the photodetector being a Raman spectrophotometer, such that the first measured signal is a Raman spectrum at the measuring depth, the method further comprising the determination of a correction term, as a function of the determined optical scattering property, the correction function comprising an exponential function, the exponent of the exponential function depending on said correction term and on said measuring depth.

According to an embodiment, the first light source is a laser source, the photodetector being a Raman spectrophotometer, such that the first measured signal is a Raman spectrum at the measuring depth, the method further comprising:
measuring, with the said Raman spectrophotometer, a depth-wise Raman spectrum, representative of an optical signal backscattered by the sample in response to the first light beam, when the said first object focal plane is situated, in the sample, at a depth from the surface, the said depth being greater than a previously determined threshold depth;
determining a correction term, as a function of the determined optical scattering property;
the correction function taking into account the said depth-wise Raman spectrum and the said correction term.

The correction function may comprise an exponential function, and preferably an increasing exponential function, the exponent of the exponential function depending on the correction term and on the measuring depth.

The correction function may comprise a product of the said Raman spectrum by the said exponential function.

This correction function may comprise an addition of the said depth-wise Raman spectrum to the said product of the said Raman spectrum at the measuring depth by the said exponential function.

According to an embodiment, the first optical signal is a fluorescence signal.

According to an embodiment, the optical scattering property is a coefficient describing the scattering of the light in the said sample, in particular a reduced scattering coefficient, a scattering coefficient or a scattering anisotropy factor.

The determination of the said optical property may include the following steps:
- performing a second illumination of a surface of the sample with a second light beam, so as to form, on said surface, an elementary illumination zone, corresponding to the part of the said surface illuminated by the said second light beam;
- detecting N second optical signals, backscattered by the sample, each second optical signal emanating from the surface of the sample at a backscattering distance from the said elementary illumination zone, N being an integer greater than or equal to 1, so as to form as many second detected signals;
- determining at least one optical scattering property of the sample, by comparison between:
  - a function of each second detected signals;
  - and a plurality of estimations of the said function of each second detected signals, each estimation being carried out by considering a predetermined value of the said optical scattering property.

At least one backscattering distance may be less than 200 µm. The method may then comprise:
- detecting at least two backscattered optical signals emanating from the surface of the sample:
  - a near backscattered optical signal, emitted at a backscattering distance of less than 200 µm;
  - a far backscattered optical signal, emitted at a backscattering distance greater than that corresponding to the said near backscattered signal, and for example greater than 200 µm;
- determining a first optical property on the basis of the near backscattered optical signal;
- determining a second optical property, different from the first optical property, on the basis of the far backscattered signal.

The method may also comprise detecting at least two near backscattered optical signals, at two different backscattering distances, the two distances being less than 200 µm.

The sample examined may be the skin of a human or of an animal.

The intensity of the backscattered optical signal may be measured at a plurality of wavelengths.

Another object of the invention is a device for characterizing a sample, comprising:
- a first light source, configured to emit a first light beam towards a surface of the said sample;
- a first optical system, configured to focus the said first light beam in an object focal plane;
- a first photodetector;
- a spatial filter, interposed between the said first optical system and the said photodetector, the said spatial filter comprising a window for transmitting a first optical signal, backscattered by the said sample when it is exposed to the said first light beam towards the first photodetector, the said window being disposed in the conjugate focal plane of the said object focal plane;
- the first photodetector being configured to output a first measured signal from said first optical signal.

The device may comprise a microprocessor, able to correct the said first measured signal, by implementing the method described above.

The device may comprise a microprocessor, being configured to apply a correction function to said first measured signal, said correction function depending on an optical scattering property of said sample.

According to an embodiment, the device may include:
- a second light source, able to emit a second light beam towards a surface of the said sample, so as to form, on the said surface, an elementary illumination zone;
- at least one detection optical fibre, extending between a proximal end, able to be coupled to a second photodetector, and a distal end, able to collect a second optical signal backscattered by the sample when it is exposed to the said second light beam;
- a second optical system comprising all or part of the first optical system, the said second optical system exhibiting a magnification factor and an optical axis;
- the said second optical system being able to conjugate the distal end of each detection optical fibre with an elementary detection zone situated on the surface of the sample;
- so that that the distance between the elementary illumination zone and each elementary detection zone, perpendicularly to the said optical axis, is dependent on the said magnification factor.

The device may include a microprocessor so as to determine an optical diffusion property according to the steps described in this specification.

In an embodiment, the second optical system is also able to conjugate the said second light source with an elementary illumination zone, situated on the surface of the sample.

The device may comprise a return or reflecting element, able to direct:
- the said first light beam towards the sample;
- or the said first optical signal backscattered by the sample towards the said first photodetector;
- or the said second light beam towards the sample;
- or the said second optical signal towards the said second photodetector.

The device may also comprise:
- a first detection optical fibre, whose distal end is situated at a first distance from the said second light beam;
- a second detection optical fibre, whose distal end is situated at a second distance from the said second light beam, the said second distance being greater than the said first distance.

The second light source may comprise an illumination optical fibre, extending between:
- a proximal end, especially able to receive light;
- and a distal end, able to emit the said second light beam in the direction of the surface of the sample.

The said first optical system and second optical system may be merged and then form a common optical system.

A detection optical fibre may be disposed in the said conjugate focal plane of the said object focal plane of the said common optical system, the said detection optical fibre being able to transmit the said first optical signal towards the first photodetector or towards the second photodetector.

The first photodetector and the second photodetector may form one and the same photodetector.

The first light source and the second light source may form one and the same light source.

DETAILED DESCRIPTION

Figure 1:
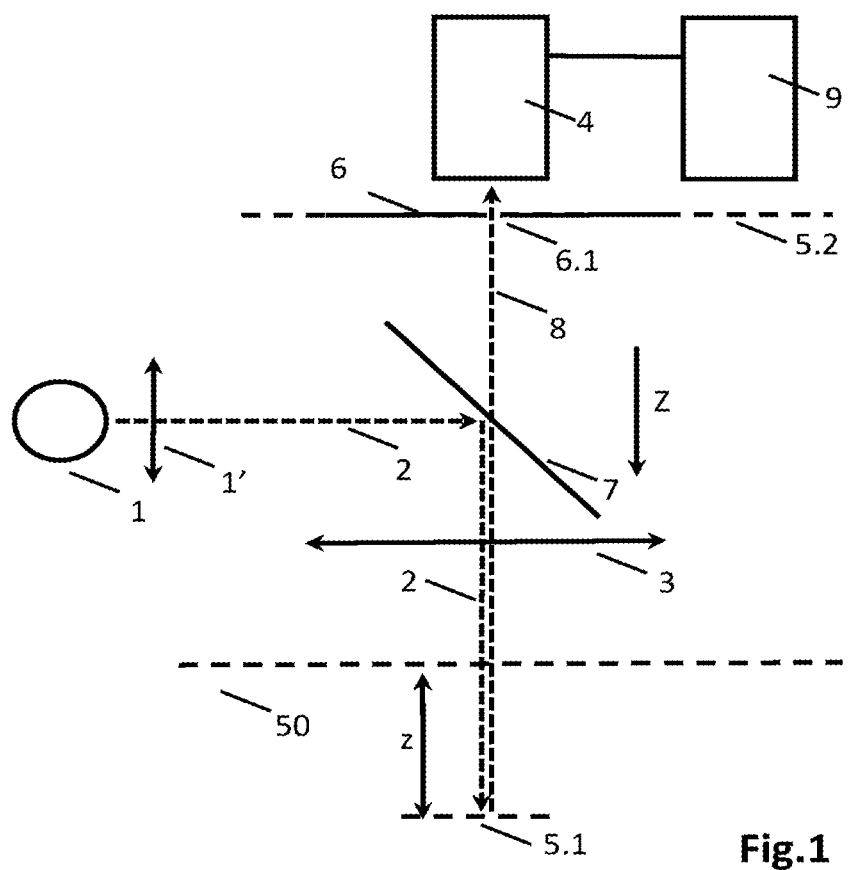
FIG. 1 represents a confocal Raman spectrometry device.

FIG. 1 represents an exemplary confocal Raman spectrometry device. It comprises a first monochromatic light source 1, typically a laser source, for example centred on a wavelength of 532 nm, able to produce a first monochromatic laser beam 2 towards the surface of an analysed sample 50.

The device also comprises a first optical system 3, able to focus the said laser beam 2 in an object focal plane 5.1, in particular inside the sample 50. The first optical system 3 exhibits an optical axis Z, preferably extending perpendicularly to the surface of the sample (50).

The laser beam is directed towards the sample 50 by a reflection on a semi-reflecting plate 7.

The device also comprises a spatial filter, in the form of a diaphragm 6, of pinhole type, whose aperture 6.1 is disposed in the image focal plane 5.2, the conjugate of the said object focal plane 5.1, as well as a first photodetector, which is here a Raman spectrophotometer 4, disposed downstream of the diaphragm 6. The term downstream is understood in the direction of propagation of light. The aperture of the pinhole is typically a few tens of µm, and preferably less than 500 µm. It is for example 50 µm.

When illuminated by the laser beam 2, the sample is able to emit a first optical signal 8, the latter being transmitted, by the semi-reflecting plate 7, towards the spectrophotometer 4. The Raman spectrophotometer 4 is able to establish a first measured signal SP, which is, in the present case, a spectrum of the first optical signal 8 backscattered by the sample, in a frequency span generally lying between a few tens of cm$^{-1}$ and a few thousands of cm$^{-1}$. The objective of the Raman spectrum is to identify the frequencies of radiations arising from energy transitions of molecules constituting the sample subsequent to inelastic scatterings with the photons constituting the incident beam.

The device comprises a microprocessor 9, coupled to the spectrophotometer 4, and from which it receives input data in the form of Raman spectra. The microprocessor comprises a programmable memory, able to store an algorithm for correcting a Raman spectrum described hereinafter. The microprocessor is able to run such algorithm.

On account of the presence of the pinhole 6 situated in the focal plane 5.2, the conjugate of the object focal plane 5.1, and disposed between the first optical system 3 and the spectrophotometer 4, only the backscattered photons, originating from the object focal plane, pass the pinhole and are detected by the Raman spectrometer, according to a so-called confocal detection configuration. The backscattered photons, originating from planes adjacent to the object focal plane 5.1, nearer to or farther from the surface of the sample, are stopped and do not contribute to the Raman spectrum formed by the spectrophotometer.

According to the axial resolution of the device, the photons originating from the immediate vicinity of the object focal plane 5.1 may also be detected. The term immediate vicinity designates a distance of a few µm, preferably less than 5 µm, from the object focal plane 5.1.

By displacing the object focal plane 5.1 in the sample, it is possible to obtain spectra representative of a succession of "optical sections", corresponding to the object focal plane.

Thus, this so-called confocal Raman spectroscopy configuration makes it possible to obtain information on the nature of the materials constituting the sample in successive planes, parallel to the surface of the sample, and extending according to a depth, so called measuring depth, of possibly as much as 100 µm to 200 µm, according to the properties regarding absorption or scattering of the light in the sample. Beyond a depth of 100 µm to 200 µm, the backscattered signal 8, carrying information, undergoes too significant an extinction, on account of the absorption or a scattering which too greatly reduces the signal passing through the pinhole. This loss in return depends on the position of the object focal plane 5.1 in the sample and the information extracted from the signal exhibits a bias.

The optical system 3 is in this example a 100× objective with numerical aperture 0.9, and focal length 1.7 mm.

A lens 1' may be coupled to the laser source, so as to tailor the diameter of the beam upstream of the optical system 3. This lens is optional.

However, the Raman signal backscattered by the sample is of low intensity. Moreover, it is attenuated by the scattering and the absorption of the photons in the depth z traversed of the sample, between the object focal plane 5.1 and the surface of the sample.

Figure 2:
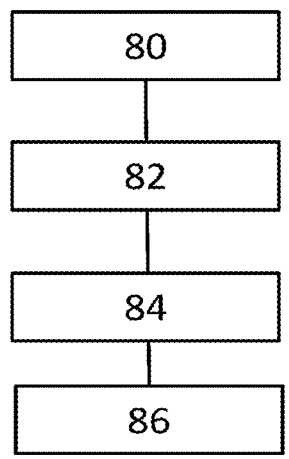
FIG. 2 represents the steps of a method for establishing a Raman spectrum correction function.

FIG. 2 represents the steps of a method for determining a correction function, denoted $F_{corr}$, able to correct the influence of the scattering of the photons in this depth z. Let us note that, with the Raman spectrophotometer being placed in a confocal configuration, the position of the analysed part of the sample is controlled, since it is the intersection of the laser beam with the object focal plane 5.1. Therefore, one knows the distance traversed by the light in the sample before and after the sample, since, in both cases, it is the depth z.

To determine this correction function, calibration phantoms have been constructed, formed from a scattering material, exhibiting optical properties, in particular a reduced scattering coefficient and a refractive index, close to that of a biological tissue. These phantoms have been produced on the basis of a material of PDMS (polydimethylsiloxane) type, by adding particles of $TiO_2$, so as to increase the scattering coefficient. Four phantoms have been constructed, exhibiting a reduced scattering coefficient $\mu_s'$ of between 21.2 cm$^{-1}$ and 55.6 cm$^{-1}$.

In a general manner, the method for establishing the correction function consists in:

establishing a plurality of spectra, termed calibration spectra $SP_{calib-z}$, by performing a scan of the object focal plane 5.1 of the optical system in a phantom, or in a plurality of phantoms, whose optical properties are close to the sample to be analysed, between the surface of the phantom (z=0) and a plane situated at a depth z of about 200 μm, and then modelling a function representative of the decay of the intensity of the Raman signal, in one or more predetermined spectral bands, termed spectral bands of interest.

The spectral bands of interest are spectral bands exhibiting spectral lines characteristic of the material constituting the phantoms, in this instance PDMS, in particular the spectral bands [680 cm$^{-1}$-720 cm$^{-1}$], [1380 cm$^{-1}$-1440 cm$^{-1}$], [2870 cm$^{-1}$-3000 cm$^{-1}$].

The first step 80 consists in obtaining the calibration spectra $SP_{calib-z}$ on the phantoms previously described, each spectrum being associated with a given depth z.

Experiment shows that, beyond a certain threshold depth $z_t$, the intensity in the said spectral bands of interest hardly evolves any longer and tends to an asymptotic value. This threshold depth $z_t$ varies as a function of the absorption properties and scattering properties of the examined material and as a function of the wavelength of the laser beam. The inventors have noted that, on the phantoms used, this asymptotic value is obtained beyond a threshold depth $z_t$=150 μm. Beyond this threshold depth, the Raman spectrum no longer evolves and tends to a Raman spectrum termed the depth Raman spectrum, denoted SP depth, depth, and such that $SP_{depth}=SP_{calib-z}$, with $z>z_t$.

Figure 3:
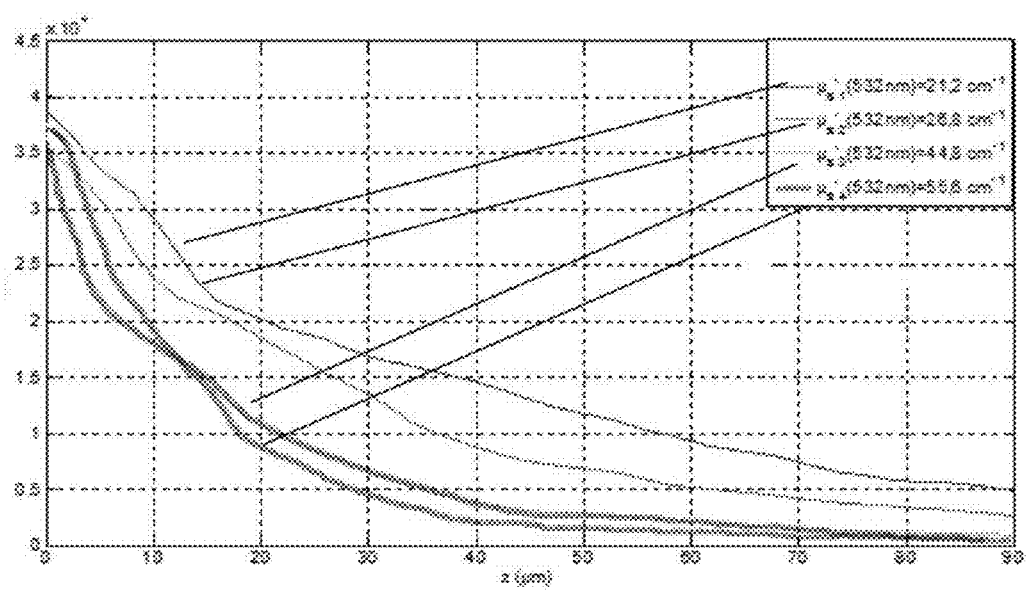
FIG. 3 represents the evolution of the intensity of a Raman signal in the spectral band 2870 cm$^{-1}$-3000 cm$^{-1}$ in a scattering medium, as a function of depth.

FIG. 3 represents the evolution of the intensity in the spectral band [2870 cm$^{-1}$-3000 cm$^{-1}$] as a function of depth z for various phantoms, whose scattering coefficient varies from 21.2 cm$^{-1}$ to 55.6 cm$^{-1}$.

A particularity of the confocal configuration described previously is that the object focal plane 5.1 of the optical system (3) is displaced inside a scattering medium, whose refractive index is different from that of air. If the sample consisted of air, the determination of the depth $z_{air}$ of the focal plane in the sample, termed the apparent depth, would readily be obtained knowing the parameters of the optical system (3). However, on account of the refractive index of the sample, the real depth z of the object focal plane 5.1 is shifted with respect to the apparent depth, in air, $z_{air}$. In order to take account of this shift, a fitting function $f_z(z)$ is determined, this forming step 82.

This step 82 is aimed at determining the apparent depth $z_{air}$ when the real depth z of the object focal plane 5.1 in the sample is known. It may be carried out by modelling or in an experimental manner. An experimental procedure is to use composite phantoms comprising:

an upper layer, whose refractive index is representative of the sample to be examined, this layer being for example formed by PDMS. Depending on the phantoms, the thickness of the upper layer is between 20 μm and 100 μm.

a lower layer, formed by a reference material whose Raman signature is known. In this example, the lower layer is formed by a silicon wafer of thickness 500 μm, silicon exhibiting a characteristic Raman spectral line at 521 cm$^{-1}$.

Each composite phantom forms the subject of a progressive scan, by displacing the object focal plane 5.1 of the optical system 3 from the upper layer towards the lower layer. When the focal plane reaches the lower layer, the intensity of the spectral line 521 cm$^{-1}$ passes through a maximum. The real depth of the focal plane, with respect to the surface of the upper layer, is then known since it corresponds to the thickness of the upper layer, while the apparent depth $z_{air}$ is known since it depends on the optical parameters of the optical system 3. A correspondence between the apparent depth $z_{air}$ and the real depth z of the object focal plane 5.1 in the sample is then effected.

By using composite phantoms the thickness of whose upper layer varies between 20 μm and 100 μm, the fitting function $f_z$ is established, making it possible to perform a fitting between the apparent depth $z_{air}$ and the real depth z.

Figure 4:
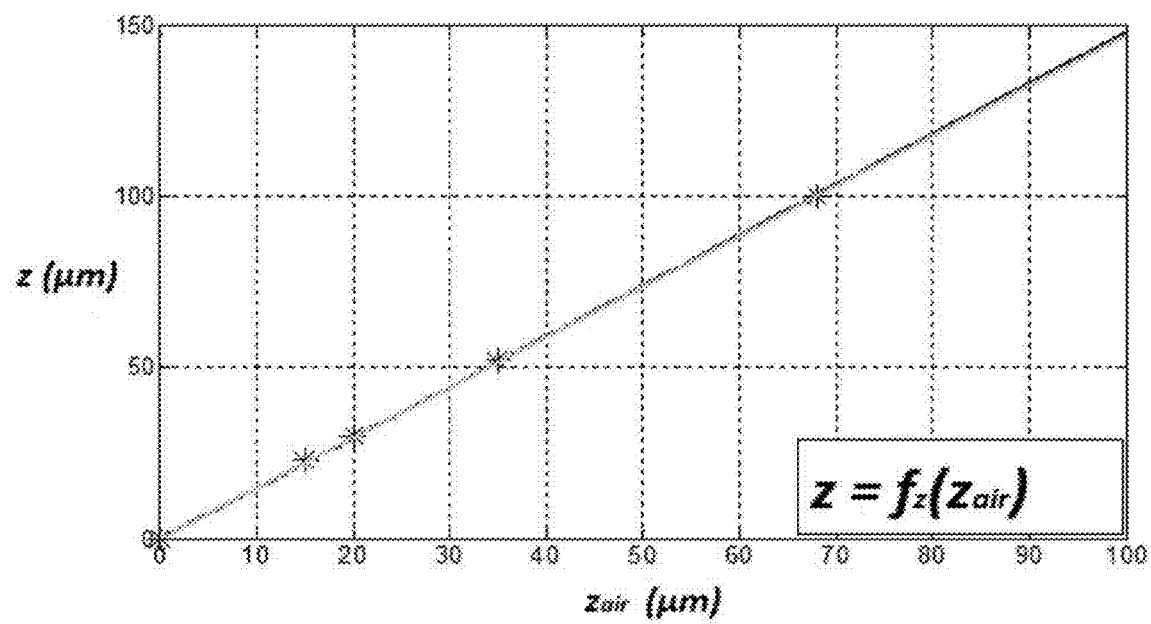
FIG. 4 represents the real depth of the object focal plane of the optical system of the device as a function of apparent depth.

FIG. 4 shows the results of an experimental calibration curve, the real depth z being represented as a function of the apparent depth $z_{air}$, on the basis of which it is possible to establish a depth fitting function $f_z$, such that $$z=f_z(z_{air})\approx 1.48\times z_{air}$$

Step 84 consists in determining a correction term β taking into account one or more optical properties of the sample. The inventors have considered that the decay in the intensity measured as a function of depth z took the form of a decreasing exponential function of the type $e^{-\beta z}$, the term β being a correction term dependent on the reduced scattering coefficient of a sample. In this example, only the reduced scattering coefficient $\mu_s'$ at the wavelength of the laser beam, i.e. λ=532 nm$^{-1}$, is considered. Indeed, the inventors have considered that the wavelengths of the backscattered beam did not deviate sufficiently from this laser wavelength to justify taking the value of the reduced scattering coefficient into account at other wavelengths. In other words, the correction function $F_{corr}$ may be based on an optical property determined at a wavelength of the beam emitted by the first light source. This optical property may be determined only at this wavelength, which simplifies the process.

The acquisitions carried out during step 80 entail the basis for modelling the decay of the intensity over several spectral bands of interest of the spectrum.

The inventors have established that, in the three spectral bands of interest defined above, the evolution of the intensity, as a function of depth z, follows the law:

$$I(z)=(I_{surface}-I_{depth})e^{-\beta\times z}+I_{depth} \qquad (1)$$

where I(z), $I_{surface}$ and $I_{depth}$ designate respectively the intensities measured, over a spectral band of interest, on the basis of the spectra $SP_{calib-z}$, $SP_{surface}$ (or $SP_{calib-z=0}$), $SP_{depth}$ (or $SP_{calib-z>zt}$).

By intensity in a spectral band is meant a value representative of the integral in the said spectral band.

The use of calibration phantoms, whose reduced scattering coefficient $\mu_s'$ varies between 211 cm$^{-1}$ and 55.6 cm$^{-1}$, makes it possible to supplement this empirical law through the following relation, expressing the dependency between the correction term β and the reduced scattering coefficient $\mu_s'$ at 532 nm:

$$\beta(\mu_s')=0.0034+8.12\ 10^{-4}\times\mu_s' \qquad (2)$$

Thus, as a first approximation, the correction term can be approximated by $$\beta(\mu_s')\approx 1.10^{-3}\times\mu_s' \qquad (2')$$

Combining expressions (1) and (2) (or (2')) makes it possible to establish a model describing the evolution of the intensity of the spectral bands of interest as a function of the depth z examined and of the scattering of the light in the sample. This is the subject of step 86.

By generalizing this model to the set of spectral bands of the spectrum, the inventors have determined a correction function $F_{corr}$ for a Raman spectrum SPz acquired at a depth z, so as to obtain a corrected Raman spectrum $SP_{corr-z}$ such that $$SP_{corr-z} = F_{corr}(SP_z) = [SP_z - SP_{depth}] e^{\beta(\mu_s') \times z} + SP_{depth} \quad (3)$$

where:
- $SP_z$ designates a spectrum measured at the depth z (that is to say at a distance z under the surface of the sample);
- $SP_{depth}$ designates a spectrum measured at a depth greater than a threshold depth $z_t$ under the surface of the sample;
- $\beta(\mu_s')$ designates the value of the correction term β as a function of the reduced scattering coefficient $\mu_s'$, at the wavelength of the incident laser beam, of the sample examined, the value of $\beta(\mu_s')$ being determined according to expression (2) or (2').

The threshold depth $z_t$ is preferably determined experimentally, on the analysed sample, by performing a plurality of measurements of spectra at various depths z, and by identifying a depth $z_t$ onwards of which the measured spectrum no longer evolves significantly, in one or more predetermined bands of interest. Indeed, this threshold depth varies as a function of the wavelength and optical properties (absorption, scattering) of the sample.

Alternatively, the threshold depth $z_t$ can be determined on calibration phantoms mimicking the optical properties of the sample to be characterized.

Naturally, expression (3) applies to the intensity IZ of any spectral band of a spectrum $SP_z$, this intensity being able to be corrected according to the expression $$I_{corr-z} = F_{corr}(I) = [I_z - I_{depth}] e^{\beta(\mu_s') \times z} + I_{depth} \quad (5),$$

where
- $I_z$ designates the intensity of a spectral band of a spectrum measured at the depth z (that is to say at a distance z under the surface of the sample);
- $I_{depth}$ designates the intensity of the said spectral band of a spectrum measured at a depth greater than a threshold depth $z_t$ under the surface of the sample;
- $\beta(\mu_s')$ designates the value of the correction term β as a function of the reduced scattering coefficient $\mu_s'$, at the wavelength of the incident laser beam, of the sample examined, $\beta(\mu_s')$ being determined according to expression (2) or (2').

Figure 5A:
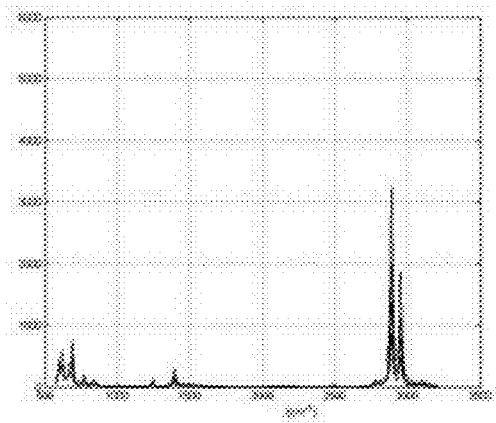
FIGS. 5A to 5D represent examples of correction of Raman spectra acquired at various depths in a known scattering medium.
Figure 5B:
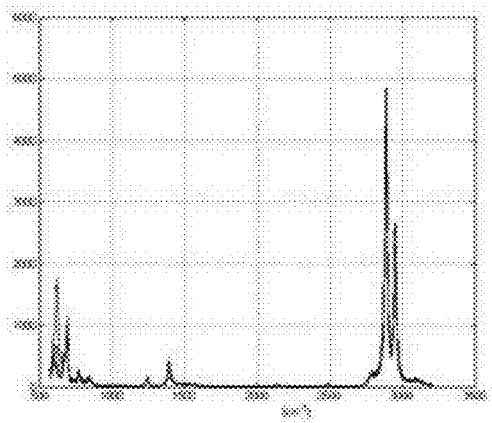

FIG. 5A represents a Raman spectrum measured on a scattering phantom of PDMS, of thickness 100 μm, and whose reduced scattering coefficient, at 532 nm, is equal to 26.8 cm$^{-1}$, with respect to a measuring depth z of 6 μm. FIG. 5B represents a Raman spectrum corrected by applying the correction function $F_{corr}$ given explicitly hereinabove. It is seen that the peaks are corrected in an effective manner.

Figure 5C:
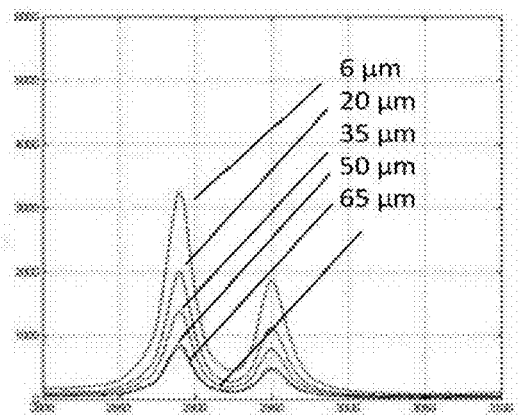
Figure 5D:
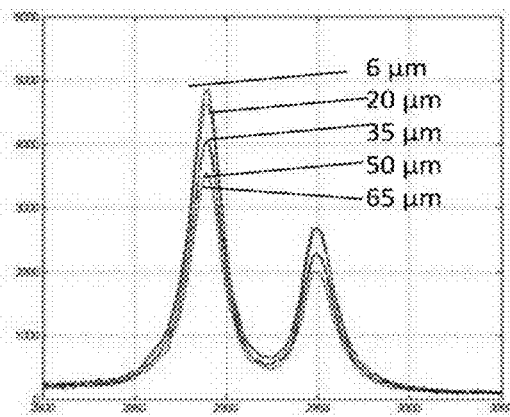

FIGS. 5C and 5D represent a zoom of spectra, highlighting respectively uncorrected and corrected over a spectral band extending between 2800 and 3050 cm$^{-1}$. Going from the most intense peak towards the least intense peak, the measuring depths z considered are respectively 6 μm, 20 μm, 35 μm, 50 μm and 65 μm. Comparison between FIGS. 5C and 5D attests to the quality of the correction.

Figure 6A:
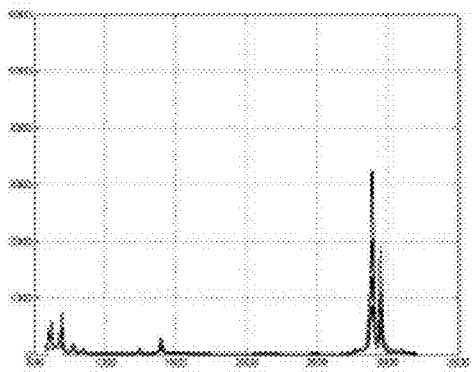
FIGS. 6A to 6D represent examples of correction of Raman spectra acquired at various depths in a known scattering medium.
Figure 6B:
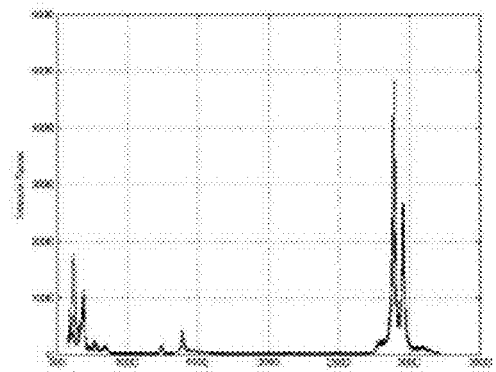

FIG. 6A represents a Raman spectrum measured on a scattering phantom of PDMS, of thickness 100 μm, and whose reduced scattering coefficient, at 532 nm, is equal to 55.6 cm$^{-1}$, for a depth z of 6 μm. FIG. 6B represents a Raman spectrum corrected by applying the correction function given explicitly hereinabove. It is seen that the peaks are corrected in an effective manner.

Figure 6C:
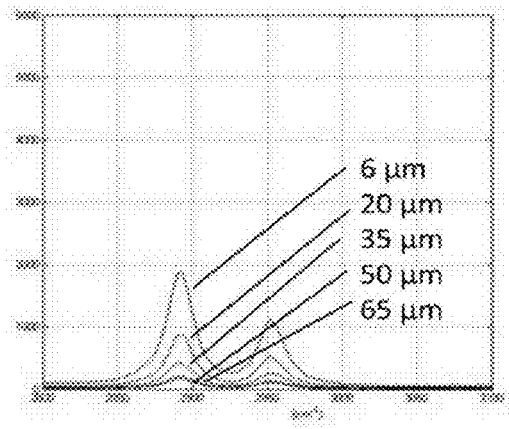
Figure 6D:
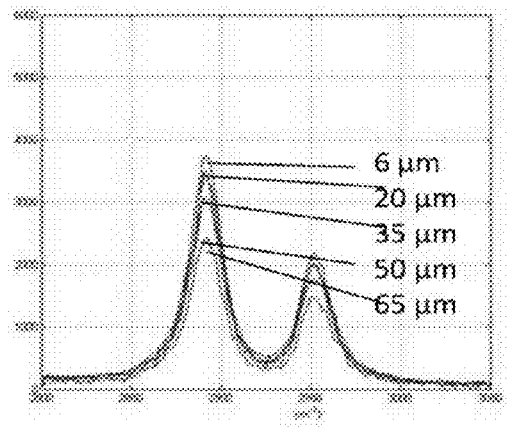

FIGS. 6C and 6D represent a zoom of spectra respectively uncorrected and corrected over a spectral band extending between 2800 and 3050 cm$^{-1}$. Going from the most intense peak towards the least intense peak, the depths considered are respectively 6 μm, 20 μm, 35 μm, 50 μm and 65 μm. Comparison between FIGS. 6C and 6D attests to the quality of the correction.

One of the significant elements of the correction is the knowledge of the optical scattering properties in the medium, in particular a coefficient describing the scattering of light in the medium, such as the reduced scattering coefficient $\mu_s'$, the scattering coefficient $\mu_s$ or the scattering anisotropy factor g.

Figure 9:
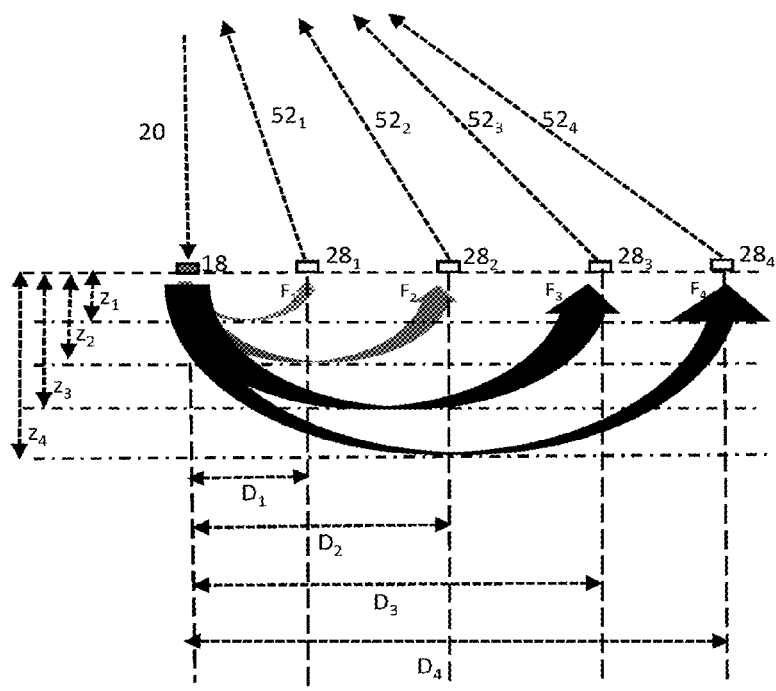
FIG. 9 represents the traversal of the light in a scattering sample as a function of the backscattering distance.

In relation to FIG. 9, such optical properties can be determined by directing a second collimated light beam 20 at the surface of the sample, so as to form, on the surface of the sample, an elementary illumination zone 18, formed by the intersection of the said second light beam with the surface of the sample. By analysing a backscattered optical signal ($S_1$, $S_2$, $S_3$, $S_4$), emanating from the surface of the sample at one or more distances (D1, D2, D3, D4), termed the backscattering distances, from the elementary illumination zone 18, it is possible to determine the optical properties of the sample.

The inventors have designed a bimodal device, combining two analysis modalities:
- A first modality, aimed at carrying out a first analysis of the sample, on the basis of a first optical signal 8 backscattered by the sample, detected by a first photodetector placed in a confocal configuration. This first optical signal 8 can be a signal carrying information of Raman type or a fluorescence signal, the objective then being to establish information as regards the construction of the sample: determination of the chemical nature of constituents (Raman spectrometry) or presence of a fluorophore (fluorescence measurement).
- A second modality, aimed at determining the optical properties of the sample, by measuring a second backscattered optical signal 52, according to the principles recalled in the previous paragraph.

The results obtained through the second modality can advantageously be used to correct the signal acquired in the course of the first modality, so as to increase the accuracy of the analysis.

Figure 7A:
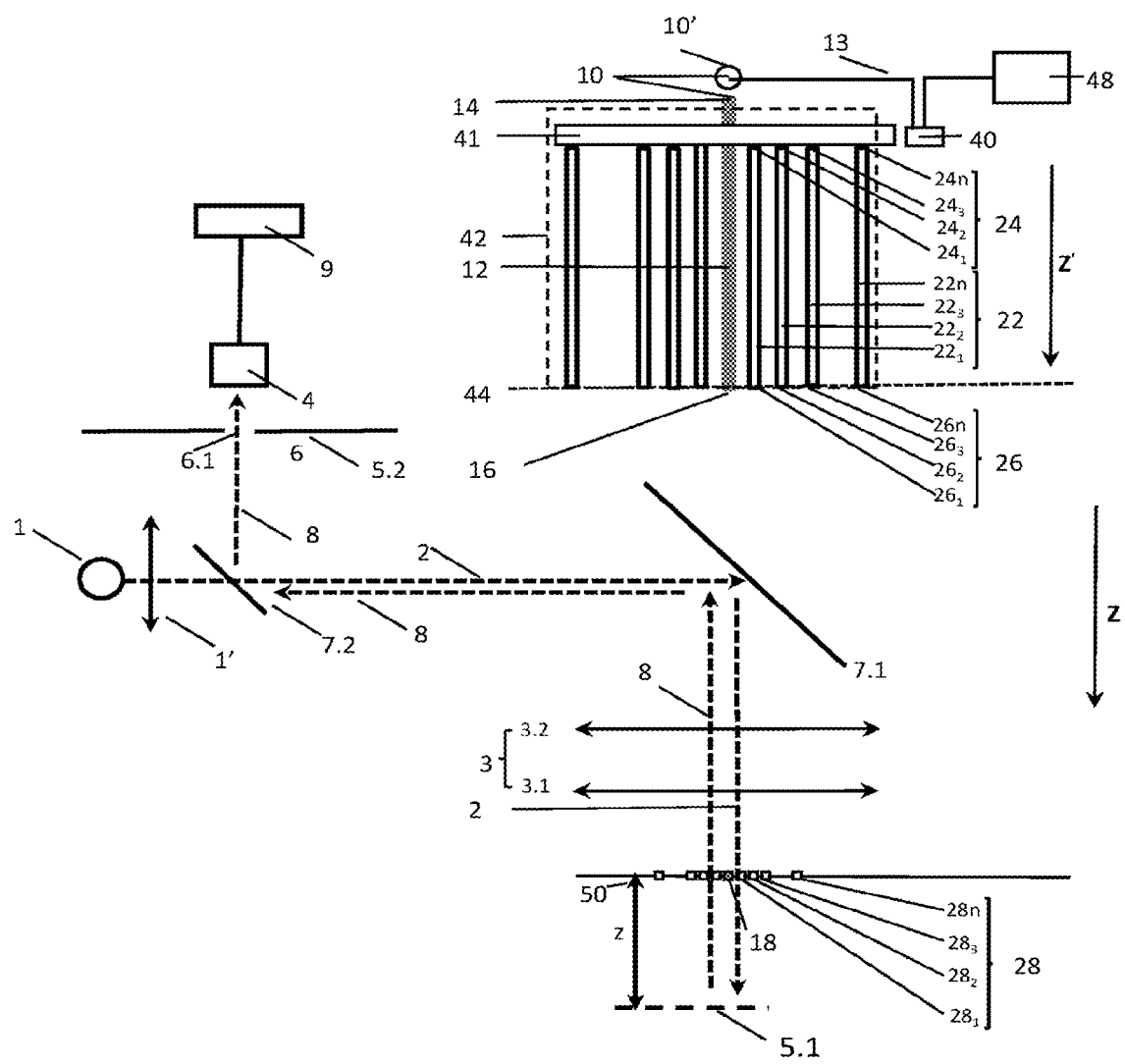
FIGS. 7A and 7B represent a first exemplary bimodal device, making it possible to combine a measurement by Raman spectrometry and a diffuse reflectance measurement.

According to one embodiment, represented in FIG. 7A, the bimodal device comprises a Raman spectrometry measurement pathway (1$^{st}$ modality), exhibiting the characteristics described in relation to FIG. 1, and also comprising a measurement pathway allowing the determination of the optical properties of the sample (2$^{nd}$ modality).

The same elements are depicted as those described in relation to FIG. 1, namely a laser radiation source 1, coupled to an optical system 3, able to focus a first optical beam 2, in this instance a laser beam, produced by the source 1 in the object focal plane 5.1 of the optical system 3, the said object focal plane 5.1 being situated at a depth z below the surface of the sample 50.

The laser beam 2 is transmitted by a first semi-reflecting plate 7.1, and is then reflected in the direction of the sample by a second semi-reflecting plate 7.2.

The optical system comprises here a microscope objective 3.1, coupled to a lens 3.2.

In response to this beam, the part of the sample situated in the vicinity of the intersection of the beam 2 with the object focal plane 5.1 emits a first optical signal 8, to be collected by the Raman spectrometer placed according to a confocal configuration, on account of the presence of the diaphragm 6, whose aperture 6.1, forming a pinhole, is disposed in the image focal plane 5.2 conjugate with the object focal plane 5.1. Note that the diaphragm 6 can be replaced by an optical fibre, of which a distal end, able to collect the first optical signal 8, is placed in the image focal plane 5.2, the proximal end of the said fibre then ensuring the transfer of the optical signal to the Raman spectrometer 4. In this case, the distal end of the optical fibre behaves in a manner equivalent to the diaphragm 6 and forms a spatial filter comprising a window, in this instance the distal end of the fibre, able to transmit the first optical signal 8 to the photodetector 4.

The microprocessor 9, coupled to the Raman spectrometer 4, ensures the processing of the Raman spectra SPz measured when the object focal plane 5.1 is placed at a depth z under the surface of the sample and in particular their correction according to the method described above.

Moreover, the device represented in FIG. 7A comprises a measurement pathway able to characterize the optical properties of the sample.

Thus, the device comprises a second light source 10, which is in this example a white light source 10'.

The second light source 10 comprises, in this embodiment, an illumination optical fibre 12, extending between a proximal end 14, and a distal end 16. The illumination optical fibre 12 is able to collect the light, through a proximal end 14, and to emit a light beam 20, so called second light beam, through a distal end 16, the said light beam then being directed towards the surface of a sample 50. In such a configuration, the light source 10 is termed fibred.

The diameter of the emission optical fibre 12 is between 100 µm and 1 mm, and is for example equal to 400 µm.

By point source is meant a source whose area is less than 1 cm$^2$, and preferably less than 5 mm$^2$, and more preferably less than 1 mm$^2$.

The device also comprises a plurality of detection optical fibres $22_1$, $22_2$, $22_3$ . . . $22_n$, the index n lying between 1 and N, N designating the number of detection optical fibres in the device. N is a natural integer generally lying between 1 and 100, and preferentially lying between 5 and 50. Each detection fibre $22_1$, $22_2$, $22_3$ . . . $22_n$ extends between a proximal end $24_1$, $24_2$, $24_3$ . . . $24_n$ and a distal end $26_1$, $26_2$, $26_3$ . . . $26_n$.

Figure 7B:
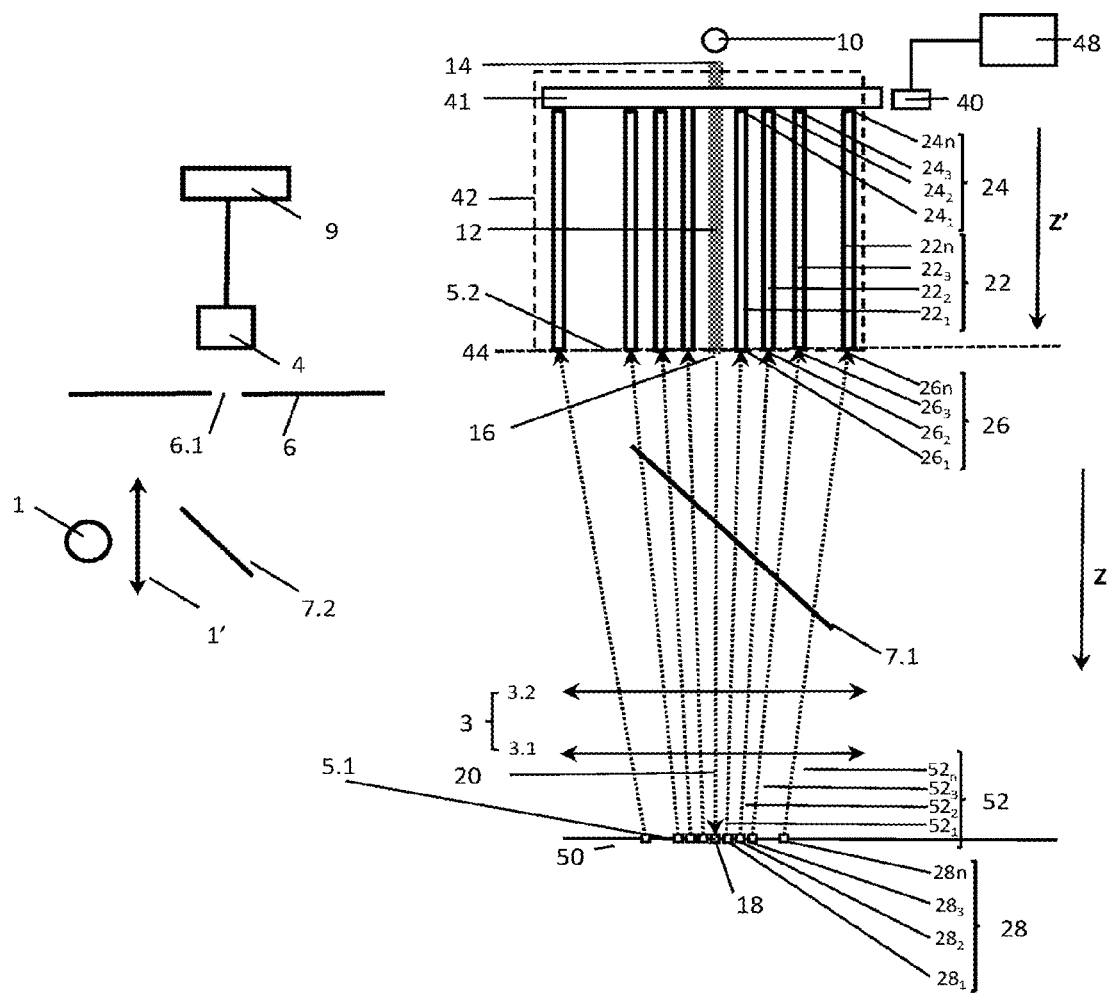

In FIGS. 7A and 7B, the references 22, 24 and 26 designate respectively the set of detection fibres, the set of proximal ends of the detection fibres and the set of distal ends of the detection fibres.

The diameter of each detection optical fibre 22 is between 50 µm and 1 mm, and is for example equal to 300 µm.

The proximal end 24 of each detection optical fibre 22 is able to be optically coupled to a second photodetector 40.

FIG. 7B represents the operation of the device according to the modality for determining the optical properties of the sample.

The distal end $26_1$, $26_2$, $26_3$ . . . $26_n$ of each detection optical fibre 22 is able to collect respectively a second optical signal $52_1$, $52_2$, $52_3$ . . . $52_n$ backscattered by the sample 50, when the latter is exposed to the light beam 20, the said optical signal being transmitted by the semi-reflecting plate 7.1.

The photodetector 40 is able to detect each second optical signal $52_1$, $52_2$, $52_3$ . . . $52_n$ so as to form a signal $S_1$, $S_2$, $S_3$, . . . $S_n$, termed the second measured signal, respectively representative of each second detected optical signal.

It may be a spectrophotometer, able to establish the wavelength spectrum of the optical signal collected by the detection optical fibre 22 to which it is coupled.

The detection optical fibres 22 extend parallel to a longitudinal axis Z', around the emission optical fibre 12. They are held fixed with respect to one another by a holding element 42. Their distal ends 26 are coplanar, and define a detection plane 44.

An optical fibre 13, termed the excitation return fibre, links the second light source 10 to the second photodetector 4. This optical fibre is useful for carrying out a calibration measurement detailed subsequently. This excitation return optical fibre is not represented in the following figures, but may be present over the whole set of embodiments.

Figure 8:
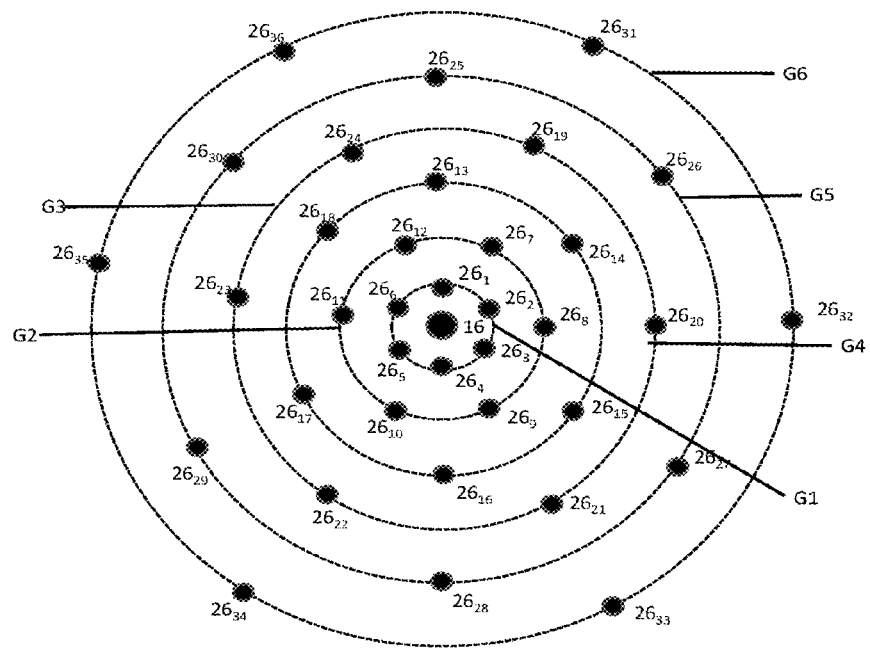
FIG. 8 represents a sectional view of the device similar to the device represented in FIGS. 7A and 7B.

FIG. 8 represents a sectional view of the device, in the detection plane 44, formed by the set of distal ends 26 of the N detection fibres. In this example, N is equal to 36. As may be seen, the detection optical fibres are distributed according to:

a first group $G_1$ of six detection optical fibres $22_1$ . . . $22_6$, disposed regularly along a circle centred on the emission optical fibre 12, in such a way that the distal end $26_1$ . . . $26_6$ of each fibre of this group is a first distance $d_1$ equal to 300 µm away from the distal end 16 of the emission optical fibre 12.

a second group $G_2$ of six detection optical fibres $22_7$ . . . $22_{12}$, disposed regularly along a circle centred on the emission optical fibre 12, in such a way that the distal end $26_7$ . . . $26_{12}$ of each fibre of this group is a second distance $d_2$ equal to 700 µm away from the distal end 16 of the emission optical fibre 12.

a third group $G_3$ of six detection optical fibres $22_{13}$ . . . $22_{18}$, disposed regularly along a circle centred on the emission optical fibre 12, in such a way that the distal end $26_{13}$ . . . $26_{18}$ of each fibre of this group is a third distance $d_3$ equal to 1.1 mm away from the distal end 16 of the emission optical fibre 12.

a fourth group $G_4$ of six detection optical fibres $22_{19}$ . . . $22_{24}$, disposed regularly along a circle centred on the emission optical fibre 12, in such a way that the distal end $26_{19}$ . . . $26_{24}$ of each fibre of this group is a fourth distance $d_4$ equal to 1.5 mm away from the distal end 16 of the emission optical fibre 12.

a fifth group $G_5$ of six detection optical fibres $22_{26}$ . . . $22_{30}$, disposed regularly along a circle centred on the emission optical fibre 12, in such a way that the distal end $26_{25}$ . . . $26_{30}$ of each fibre of this group is a fifth distance $d_5$ equal to 2 mm away from the distal end 16 of the emission optical fibre 12.

a sixth group $G_6$ of six detection optical fibres $22_{31}$ . . . $22_{36}$, disposed regularly along a circle centred on the emission optical fibre 12, in such a way that the distal end $26_{31}$ . . . $26_{36}$ of each fibre of this group is a sixth distance $d_6$ equal to 2.5 µm away from the distal end 16 of the emission optical fibre 12.

When speaking of a distance between two fibres, or between a fibre or a light beam, a centre to centre distance is meant.

Thus, each distal end 26n of a detection optical fibre 22n is placed, in a plane perpendicular to the longitudinal axis Z' according to which these fibres extend, at a distance $d_n$ from the second light source 10 (that is to say from the distal end 16 of the emission fibre 12), and, consequently, at a distance $d_n$ from the light beam 20 directed towards the sample 50.

The device can comprise a second photodetector 40, able to be coupled to the proximal end $24_n$ of each detection optical fibre $22_n$. In this example, the second photodetector is a spectrophotometer, able to determine the spectrum of a second optical signal $52_1$ . . . $52_n$ backscattered by the sample when the latter is exposed to the second light beam 20. Accordingly, the proximal ends 24 of each group of detection optical fibres, described hereinabove, are grouped together and are, group by group, successively coupled to the second photodetector 40 by means of an optical switch 41.

Thus, the second photodetector makes it possible to measure the radiation 52 backscattered by the sample, under the effect of an illumination by the second light beam 20.

The second photodetector 40 is able to be connected to a second microprocessor 48, the latter being configured to implement the method to determine an optical property of the sample. Alternatively, the device comprises only a single microprocessor 9, able to be coupled to the first photodetector 4 and to the second photodetector 40. In this case, the microprocessor 9 performs the operations of correcting the Raman spectrum and of determining the optical properties.

The optical system 3 exhibits a magnification factor G and an optical axis Z. In this example, the optical axis Z coincides with the longitudinal axis Z' according to which the detection optical fibres extend, thereby constituting a preferred configuration. In this example, the optical system 3 comprises:
- a microscope objective 3.1, placed in infinite focus configuration, able to produce an image at infinity of the surface of the observed sample, when the latter is placed at the focus of this objective. In this example, this entails a 100× objective, of focal length $f_1=1.7$ mm,
- an achromat doublet 3.2, of focal length $f_2=50$ mm, able to project the image provided by the latter into the detection plane 44, this plane being placed at a distance equal to the focal length of the doublet.

The optical system 3 described hereinabove exhibits a magnification factor G equal to the ratio of the focal lengths, i.e. $G\approx 30$. Preferably, the magnification factor G is greater than 2, or indeed greater than 3 or 5.

Preferably, the optical system 3 is removable and interchangeable, thereby allowing, by using the same device, the use of optical systems exhibiting different magnification factors.

In the first modality, aimed at establishing a Raman spectrum, the object focal plane 5.1 of the optical system 3 is situated in the sample, at a measuring depth z from the surface of the sample.

In this second modality, aimed at establishing the optical properties of the sample, the object focal plane 5.1 of the optical system coincides with the surface of the sample. It then makes it possible to form an image of the surface of the sample 50 on the detection plane 44 formed by the distal ends 26 of each detection optical fibre 22, with a given magnification factor G. Thus, each distal end $26_1, 26_2 \ldots 26_n$ is respectively conjugated with an elementary detection zone $28_1, 28_2 \ldots 28_n$ of the surface of the sample. In this manner, each detection optical fibre $22_1, 22_2, \ldots 22_n$ is able to collect respectively a second elementary optical signal $52_1, 52_2, \ldots 52_n$ backscattered by the sample, each elementary optical signal $52_1, 52_2, \ldots 52_n$ emanating respectively from the elementary detection zone $28_1, 28_2 \ldots 28_n$. Each elementary detection zone is preferably distinct from the elementary detection zone, and is separated from the latter by a non-zero distance.

Likewise, the distal end 16 of the emission fibre 12 is conjugated with an elementary illumination zone 18 on the surface of the sample, this elementary illumination zone constituting the point of impact of the light beam 20 on the surface of the sample 50.

Thus, whatever the embodiment, each of the said distal ends $26_1, 26_2 \ldots 26_n$ can be situated in an image focal plane of the optical system 3, and conjugated with an elementary detection zone $28_1, 28_2 \ldots 28_n$ situated in the object focal plane of the said optical system, on the surface of the sample.

Likewise, the distal end 16 of the emission fibre 12 is conjugated with an elementary illumination zone 18 on the surface of the sample, this elementary illumination zone constituting the point of impact of the second light beam 20 on the surface of the sample 50.

In a general manner, and whatever the embodiment, the term elementary zone designates a part of the surface of the sample whose dimensions are sufficiently small to consider that it is traversed by a homogeneous light radiation. Stated otherwise, an elementary zone is a zone of delimited shape, preferably pointlike, that is to say whose diameter or diagonal is less than 5 mm, and preferably less than 1 mm, or indeed less than 500 μm.

An elementary illumination zone 18 is traversed by the light beam 20, propagating in the direction of the sample 50, while an elementary detection zone $28n$ is traversed by a backscattered radiation $52n$, this radiation being produced by the backscattering, in the sample, of the light beam 20. The optical coupling, carried out by the optical system 3, allows each detection fibre $22_n$ to collect the elementary backscattered radiation $52n$, the latter corresponding to the backscattered radiation traversing the elementary zone $28n$. Preferably, each elementary detection zone $28n$ does not overlap an elementary illumination zone 18.

The holding element 42 can ensure a rigid link between the detection optical fibres 22 and the optical system 3, so as to hold the detection plane 44, formed by the distal ends 26 of the detection optical fibres, at a fixed distance from the optical system 3.

If $d_n$ represents the distance between the distal end $26n$ of a detection fibre $22n$ and the distal end 16 of the emission fibre 12, distance calculated in a plane perpendicular to the optical axis Z, the distance $D_n$ between the elementary detection zone $28n$, the conjugate of the said distal end $26n$, and the elementary illumination zone 18, the conjugate of the said distal end 16, is such that:

$$Dn = \frac{dn}{G}$$

The distance $D_n$ is called backscattering distance, since it corresponds to the distance, in a plane perpendicular to the optical axis Z, between the elementary illumination zone 18 and an elementary detection zone $28n$ from which the backscattered signal Sn emanates.

If the distance between the light beam and the distal end of a detection optical fibre is, upstream of the optical system, equal to a first distance, the backscattering distance is, at the surface of the sample, equal to the said first distance weighted by the inverse of the magnification factor.

When its magnification factor is greater than 1, which is the preferred embodiment, the optical system 3 tends to bring the elementary detection zones $28n$ significantly closer to the elementary illumination zone 18. The term "upstream" is understood by considering the direction of propagation of the light.

When the magnification factor G is less than 1, the optical system tends on the contrary to move the elementary detection zones $28n$ significantly further from the elementary illumination zone 18 with respect to the configuration of the prior art.

Thus, depending on the value of the magnification factor, the elementary detection zones 28n are:
- either brought closer together, and brought closer to the elementary illumination zone, their surface area also being decreased by the square of the magnification factor, with respect to the surface area of the distal end with which they are respectively associated. This makes it possible to perform a characterization of the sample with a high spatial resolution, on a smaller depth than according to the prior art.
- or moved further apart, and moved away from the elementary illumination zone, their surface area being increased by the square of the magnification factor, with respect to the surface area of the distal end with which they are respectively associated. This makes it possible to perform a characterization of the sample with a lower spatial resolution.

FIG. 9 summarizes this technical effect, each arrow $F_1$, $F_2$, $F_3$ and $F_4$ representing the path, in the sample 50, of the photons contributing to the respective backscattered signals $52_1$, $52_2$, $52_3$, $52_4$ respectively associated with the elementary detection zones $28_1$, $28_2$, $28_3$, $28_4$. The higher the separation between the elementary detection zones $28_1$, $28_2$, $28_3$, $28_4$ and the elementary illumination zone 18, the bigger the examined depth $z_1$, $z_2$, $z_3$, $z_4$ of the sample. Conversely, the smaller the separation between the elementary detection zones and the elementary illumination zone, the smaller the examined depth of the sample.

In the present case, the device is implemented to determine the optical properties of the sample, in particular in a superficial layer, extending between the surface of the sample and a maximum depth of about 100 µm to 150 µm, so as to use the said optical properties to perform a correction of a confocal Raman spectrum.

Hence, an optical system 3, whose magnification factor is greater than 1, and preferably greater than 5 or 10, is preferably used so as to be able to determine an optical property representative of this superficial layer.

When the second photodetector 40 is a spectrometer, the device makes it possible to perform measurements of the backscattered spectrum according to backscattering distances of a few tens to about 200 µm. One speaks of diffuse microreflectance spectroscopy.

A method is now described which is capable of being implemented by the device described above, in order to estimate one or more optical properties of the sample examined, and more particularly of a superficial layer of this sample, this layer extending in particular between the surface and a depth of generally less than 150 µm.

The term optical property designates especially a factor governing the absorption and the scattering of photons in the scattering medium, in particular an absorption coefficient, a scattering coefficient, a reduced scattering coefficient, a scattering anisotropy coefficient.

Figure 10:
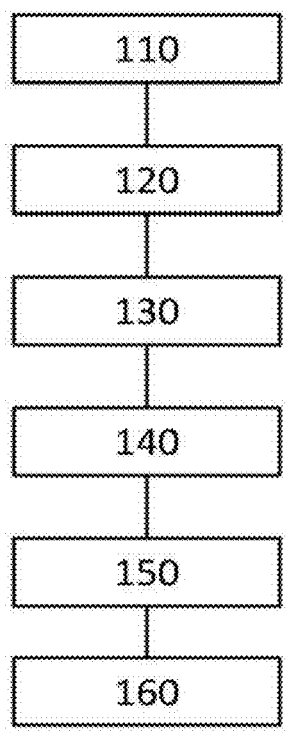
FIG. 10 represents the steps of a method for determining the optical properties of a sample that are able to be implemented with the aid of a device according to the invention.

In relation to FIG. 10, the main steps of a method allowing the estimation of the optical scattering properties, in particular the absorption coefficient pa and the reduced scattering coefficient $\mu'_s$, are described. In this example, the magnification factor G rises to 30. As represented in FIG. 8, the device comprises 36 detection fibres, divided into 6 groups of 6 fibres, as a function of the distance $d_n$ separating each detection fibre 22n from the illumination beam 50. These distances $d_n$ rise respectively to 300 µm; 700 µm; 1.1 mm; 1.5 mm; 2 mm; 2.5 mm.

By virtue of the optical system 3, each detection fibre $22_n$ is conjugated with an elementary detection zone 28n. The elementary detection zones are then themselves divided into 7 groups, as a function of the backscattering distance $D_n$ separating each elementary detection zone 28n from the elementary illumination zone 18. Having regard to the magnification factor of the optical system 3, the distances $D_n$ rise respectively to about 10 µm; 23 µm; 37 µm; 50 µm; 67 µm; 83 µm.

The following steps are then undertaken:

$1^{st}$ step 110: application of the device previously described, facing the sample 50, in such a way that the examined surface is placed in the object focal plane 5.1 of the optical system 3.

$2^{nd}$ step 120: illumination of the sample by directing the second light beam 20 against the surface of the sample, the part of the surface illuminated constituting the illuminated elementary zone 18.

$3^{rd}$ step 130: collection of a second optical signal $52_1$, $52_2$, $52_3$, $52_4$ ... $52_n$ respectively backscattered by the sample, at the level of each elementary detection zone $28_1$, $28_2$, $28_3$, $28_4$ ... $28_n$, by the detection optical fibre $22_1$, $22_2$, $22_3$, $22_4$ ... $22_n$ whose distal end $26_1$, $26_2$, $26_3$, $26_4$ ... $26_n$ is conjugated with the said elementary zone $28_1$, $28_2$, $28_3$, $28_4$ ... $28_n$.

$4^{th}$ step 140: measurement, with the aid of a second photodetector 40, of the second measured signal Sn representative of each backscattered optical signal $52_n$ at each distance $D_n$ from the elementary illumination zone. The signal Sn can in particular be established by aggregating the optical signals collected by the detection optical fibres of one and the same group.

5th step 150: with the aid of each second measured signal $S_n$ corresponding to a backscattering distance $D_n$, determination of a function $R_n$ called the reflectance of the signal, this reflectance being obtained as a function of the signal Sn and of calibration parameters. Thus, $R_n = f_{calib}(S_n)$, or $f_{calib}$ designates a calibration function, dependent on the instrumentation implemented, for example the effectiveness of collection by the fibres, the response function of the detector and the intensity of the incident light beam. The calibration function $f_{calib}$ can be obtained in the course of a calibration phase, previously or subsequent to the measurement on the sample.

For example, the reflectance $R_n$ can be obtained, on the basis of $S_n$, according to the expression:

$$R_n = f_{calib}(S_n) = \frac{S_n - S_{ref}}{S_{source}}$$

or according to the expression $$R_n = f_{calib}(S_n) = \frac{S_n - S_{ref}}{S_{source}} \times \frac{R_{std-n}}{S_{std-n}}$$

where:
- $S_n$ is the detected signal corresponding to the distance $D_n$ of the elementary illumination zone,
- $S_{ref}$ is a calibration signal, conveying the parasitic reflections of the optical system, and obtained by activating the light source, but without the sample being present, the latter being replaced with an absorbent element, such as a black screen,
- $S_{source}$ is the signal produced by the light source,
- $S_{std-n}$ is a backscattering signal measured, by considering a backscattering distance $D_n$, on a phantom, whose optical properties (absorption, scattering) are known, by using the same device as that implemented to acquire the signal Sn, $R_{std-n}$ is an estimation of the reflectance produced, by the said phantom, at the backscattering distance $D_n$.

In a general manner, the reflectance represents the intensity of the backscattered signal. It is normalized by the intensity of the incident beam at the detector, in which case it represents a fraction of the incident beam backscattered at the backscattering distance considered.

6$^{th}$ step 160: for at least one wavelength λ, and by considering at least two backscattering distances $D_n$, determination of the pair $(\mu_a(\lambda), \mu'_s(\lambda))$ exhibiting the least disparity between the reflectance measured $R_n(\lambda)$, at the wavelength λ, and a reflectance $R_{n,\mu a,\mu s'}^{model}(\lambda)$ modelled for various values of $\mu_a(\lambda)$ and of $\mu'_s(\lambda)$, at a backscattering distance $D_n$. This determination can be carried out by minimizing a quadratic disparity, and for example according to the expression:

$$(\mu_a(\lambda), \mu'_s(\lambda)) = \mathrm{argmin}_{(\mu_a(\lambda),\mu'_s(\lambda))} \left( \sum_{n=1}^{N} \left( R_{n,\mu a,\mu s'}^{model}(\lambda) - R_n(\lambda) \right)^2 \right)$$

where:

N designates the number of distances taken into account $R_{n,\mu a,\mu s}^{model}$ is a modelled reflectance function, established for the backscattering distance $D_n$, and for a pair of values $\mu_a$ and $\mu_s'$.

The various values of modelled reflectance $R_{n,\mu a,\mu s}^{model}$ are obtained, for a plurality of pairs of values $\mu_a$, $\mu_s'$ in the course of a calibration phase, by numerical simulation, or experimentally, on gauge samples whose optical properties are known.

Figure 11:
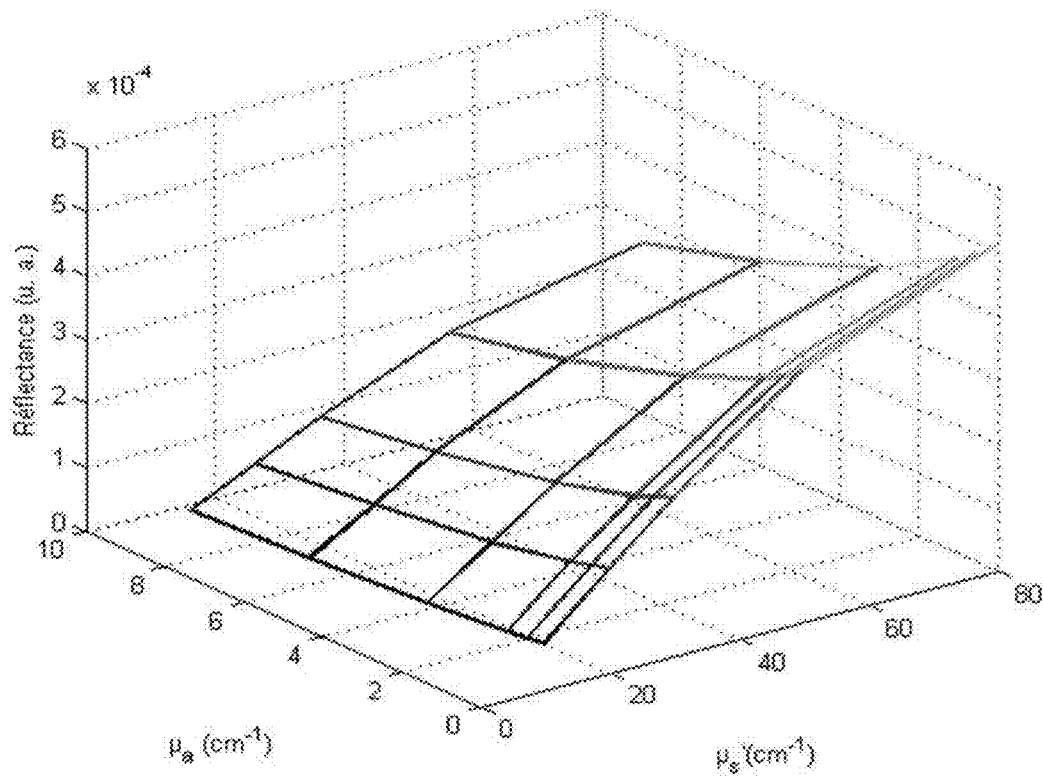
FIG. 11 is an exemplary calibration table that can be used in the method for determining the optical properties of a sample.

For a given backscattering distance $D_n$, it is possible to represent a plurality of reflectances $R_{n,\mu a,\mu s}^{model}$ modelled as a function of μa and of μs'. FIG. 11 gives an exemplary representation of such modelled reflectances at a backscattering distance of 185 μm, in the form of a calibration table, or LUT, the acronym standing for Look Up Table. Each point of the sheet represented in FIG. 11 corresponds to an estimation of the reflectance, at the said backscattering distance, as a function of the absorption coefficient $\mu_a$ and the value of the reduced scattering coefficient $\mu_s'$.

In a general manner, the notation $R_{n,p}^{model}$ designates a reflectance modelled at the backscattering distance $D_n$, by taking into account predetermined values of at least one optical parameter p. The parameter p can correspond to an optical property, for example μs', or a set of optical properties, for example (μa, μs').

The optical properties determined, and in particular $\mu_s'$, can then be used to determine the function for correction of a Raman spectrum, by way of the correction factor β, according to expression (2).

Steps 150 and 160 are implemented by the microprocessor 48 (or by the microprocessor 9 if appropriate), previously programmed for this purpose, and whose input data are the measurements carried out by the second photodetector 40.

When the second photodetector 40 is provided with a spectrometric function, the methods described above can be implemented for a plurality of different wavelengths or spectral bands. In this case, the various optical properties are obtained as a function of the wavelength or of the spectral band considered.

In the application envisaged, the use of a spectrometric detector is not rendered necessary, in so far as a determination of the optical properties at one wavelength is sufficient, in this instance the wavelength of the laser source 1, in this instance 532 nm.

Figure 12:
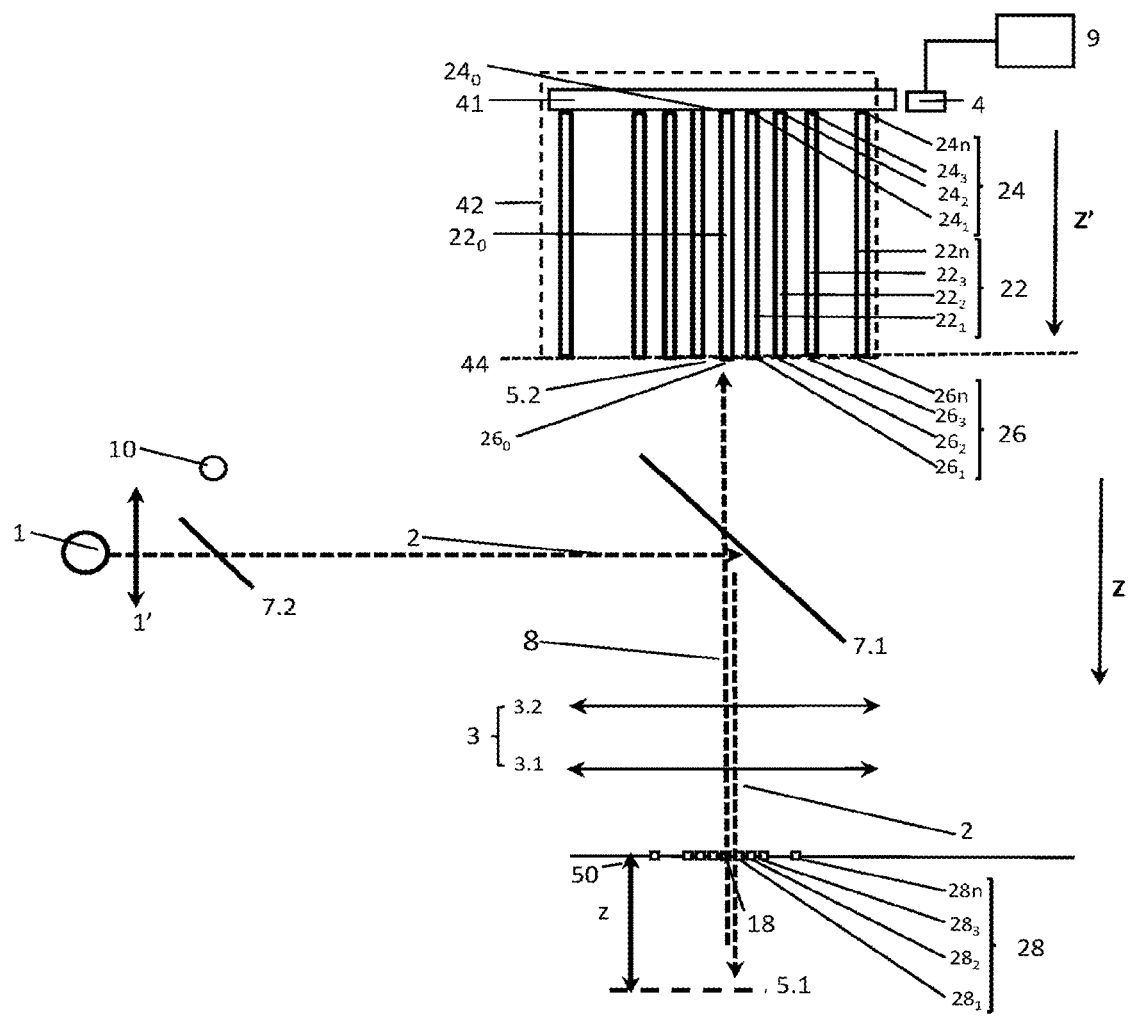
FIGS. 12 and 13 are a second and a third exemplary confocal Raman bimodal spectrometry device.

According to another embodiment, represented in FIG. 12, the second light source 10 is disposed facing the semi-reflecting plate 7.2. The second light beam is reflected by the second semi-reflecting plate 7.2, and then by the first semi-reflecting plate 7.1 in the direction of the sample.

The benefit of this configuration is that it makes it possible to collect an optical signal backscattered at an angle of 180°, that is to say backscattered parallel to the light beam 20, transmitted by the semi-reflecting plate 19 towards a detection optical fibre 22$_0$, coaxial with the said light beam 20, this optical fibre being conjugated with the elementary illumination zone 18 formed by the trace of the illumination beam 20 on the surface of the sample.

This detection fibre 22$_0$ can also be coupled, by its proximal end 24$_0$, to the Raman spectrometer 4. The focal plane 44 constitutes the image focal plane 5.2 of the optical system 3. Thus, the distal end 26$_0$ of this detection fibre 22$_0$ acts as spatial filter 6, and, in a manner equivalent to a pinhole, places the Raman spectrometer 4 in a confocal configuration. The window 6.1 of the spatial filter 6 then corresponds to the core of the said fibre, collecting the first optical signal.

Another advantage of this embodiment is that it makes it possible to replace, in an optional manner, the first photodetector 4 and the second photodetector 40 as one and the same common photodetector.

Figure 13:
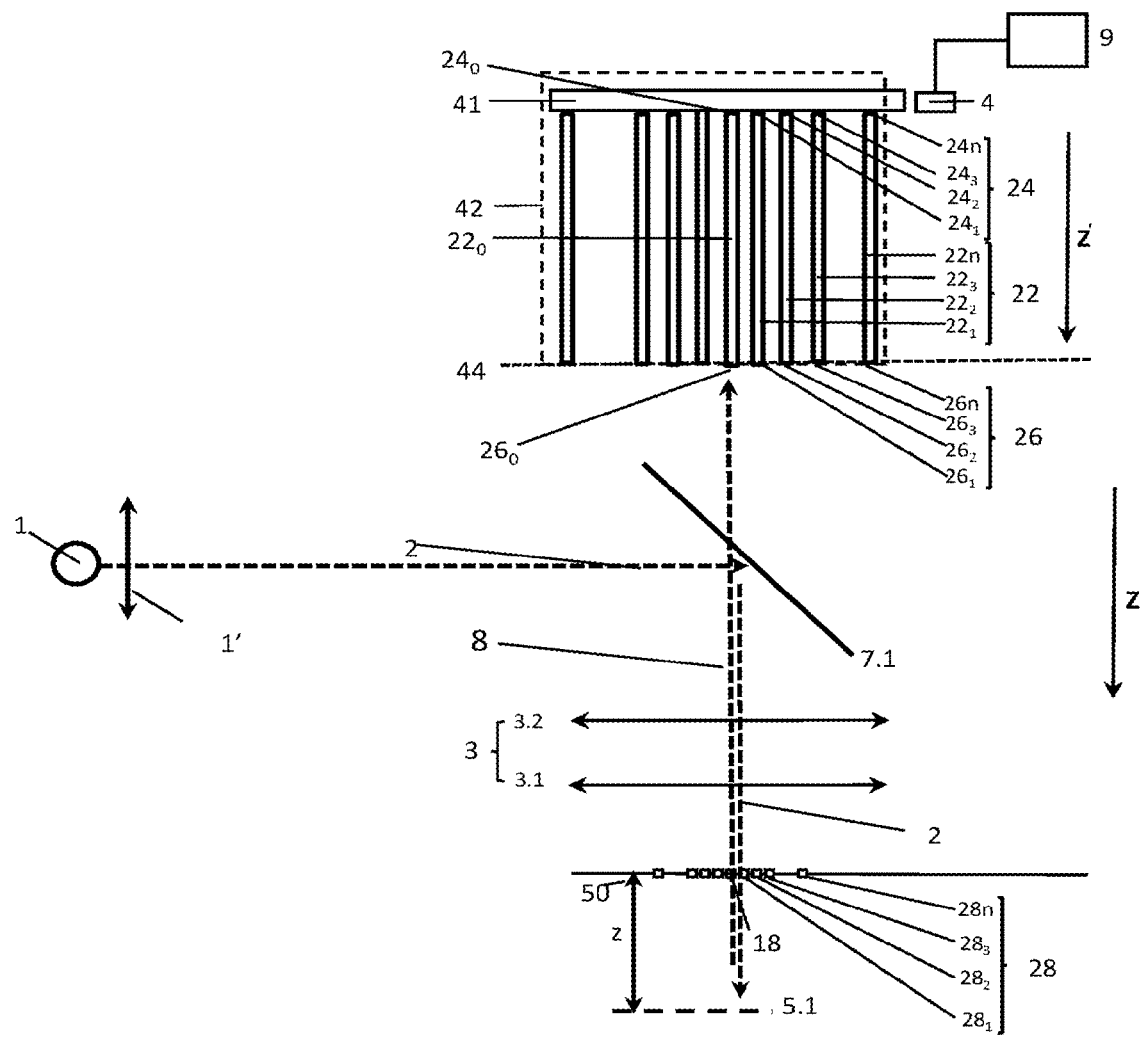

According to another embodiment, represented in FIG. 13, the laser source 1 is used as light source for the two modalities, namely the acquisition of the Raman spectrum and the determination of the optical properties of the sample. Indeed, as mentioned previously, the inventors have considered that the knowledge of the optical properties, in particular the scattering coefficient μs', at the wavelength of the laser beam alone, made it possible to perform a correction of the Raman spectrum in an effective manner.

Thus, the bimodal device can comprise just a single light source, thereby allowing a simplification of the device.

The invention claimed is:

1. A method for correcting an optical signal produced by a sample comprising the following steps:

illuminating a surface of the sample by a first light beam, produced by a first light source, said first light source being coupled to a first optical system, focusing said first light beam in an object focal plane of the first optical system, said object focal plane being situated, in the sample, at a measuring depth z from the surface of the sample; and measuring, with a first photodetector, of a first optical signal backscattered by the sample in response to the first light beam, the first photodetector producing a first measured signal representative of said first optical signal, a spatial filter being interposed between the first optical system and the first photodetector, the spatial filter comprising a window which transmits said first optical signal towards said first photodetector, the window being disposed in a conjugate focal plane of the object focal plane of the first optical system, wherein the method also comprises the following steps:
determining an optical scattering property of the sample;
applying a correction function to the first measured signal so as to generate a first corrected signal, said correction function taking into account said optical scattering property, and
wherein the determination of the optical scattering property of the sample further comprises:
performing a second illumination of a surface of the sample with a second light beam, so as to form, on said surface, an elementary illumination zone, corresponding to the part of said surface illuminated by said second light beam;
detecting N second optical signals, backscattered by the sample, each second optical signal emanating from the surface of the sample at a backscattering distance from said elementary illumination zone, N being an integer greater than or equal to 1, so as to form as many second detected signals; and
determining at least one optical scattering property of the sample, by comparison between:
a function of each second detected signals, and
a plurality of estimations of said function of each second detected signals, each estimation being carried out by considering a predetermined value of said optical scattering property.

2. The method according to claim 1, further comprising determining said measuring depth between the first object focal plane of the first optical system and the surface of the sample, wherein the correction function takes the measuring depth into account.

3. The method according to claim 1, wherein the first light source is a laser source, the photodetector being a Raman spectrophotometer, such that the first measured signal is a Raman spectrum at the measuring depth, the method further comprising the determination of a correction term, as a function of the determined optical scattering property, the correction function comprising an exponential function, the exponent of the exponential function depending on said correction term and on said measuring depth.

4. The method according to claim 1, wherein the first light source is a laser source, the photodetector being a Raman spectrophotometer, such that the first measured signal is a Raman spectrum at the measuring depth, the method further comprising:
measuring, with said Raman spectrophotometer, a depthwise Raman spectrum, representative of an optical signal backscattered by the sample in response to the first light beam, when said first object focal plane is situated, in the sample, at a depth from the surface, said depth being greater than a previously determined threshold depth;
determining a correction term, as a function of the determined optical scattering property; and
the correction function taking into account said depthwise Raman spectrum and said correction term.

5. The method according to claim 4, wherein the correction function comprises an exponential function, the exponent of the exponential function depending on the correction term and on the measuring depth.

6. The method according to claim 5, wherein the correction function comprises a product of the Raman spectrum at the measuring depth by said exponential function.

7. The method according to claim 5, wherein the correction function comprises an addition of the depth-wise Raman spectrum to the product of said Raman spectrum at the measuring depth by the exponential function.

8. The method according to claim 1, wherein the first optical signal is a fluorescence signal.

9. The method according to claim 1, wherein the optical scattering property is a coefficient describing the scattering of the light in said sample, including a reduced scattering coefficient, a scattering coefficient or a scattering anisotropy factor.

10. The method according to claim 1, in which at least one backscattering distance is less than 200 µm.

11. A device for characterizing a sample, comprising:
a first light source, configured to emit a first light beam towards a surface of said sample;
a first optical system, configured to focus said first light beam in an object focal plane;
a first photodetector;
a spatial filter, interposed between said first optical system and said photodetector, said spatial filter comprising a window for transmitting a first optical signal, backscattered by said sample when it is exposed to said first light beam towards the first photodetector, said window being disposed in the conjugate focal plane of said object focal plane;
the first photodetector being configured to output a first measured signal from said first optical signal;
a microprocessor, being configured to apply a correction function to said first measured signal, said correction function depending on an optical scattering property of said sample;
a second light source, able to emit a second light beam towards a surface of said sample, so as to form, on said surface, an elementary illumination zone;
at least one detection optical fibre, extending between a proximal end, coupled to a second photodetector, and a distal end, configured to collect a second optical signal backscattered by the sample when it is exposed to said second light beam; and
a second optical system comprising all or part of the first optical system, said second optical system exhibiting a magnification factor and an optical axis,
wherein said second optical system conjugates the distal end of each detection optical fibre with an elementary detection zone located on the surface of the sample so that the distance between the elementary illumination zone and each elementary detection zone, perpendicularly to said optical axis, is dependent on said magnification factor.

12. The device according to claim 11, wherein the second optical system is also able to conjugate the second light source with an elementary illumination zone, located on the surface of the sample.

13. The device according to claim 11, also comprising a reflecting element, able to direct:
the first light beam towards the sample;
or the first optical signal backscattered by the sample towards the first photodetector;
or the second light beam towards the sample;
or the second optical signal towards the second photodetector.

14. The device according to claim 11, also comprising
a first detection optical fibre, whose distal end is situated at a first distance from the second light beam; and
a second detection optical fibre, whose distal end is situated at a second distance from the second light beam, the second distance being greater than said first distance.

15. The device according to claim 11, wherein the second light source comprises an illumination optical fibre, extending between
- a proximal end, configured to receive the second light beam;
- and a distal end, configured to emit the second light beam towards the surface of the sample.

16. The device according to claim 11, wherein the first optical system and second optical system are merged and form a common optical system.

17. The device according to claim 16, wherein a detection optical fibre is disposed in said conjugate focal plane of said object focal plane of said common optical system, said detection optical fibre being configured to transmit the said first optical signal towards the first photodetector or towards the second photodetector.

18. The device according to claim 16, wherein the first photodetector and the second photodetector form one and the same photodetector.

19. The device according to claim 16, wherein the first light source and the second light source form one and the same light source.

20. A method for correcting an optical signal produced by a sample comprising the following steps:
- determining a threshold depth of the sample;
- measuring, with a Raman spectrophotometer, a depth-wise Raman spectrum, representative of an optical signal backscattered by the sample in response to a first light beam, when a first object focal plane is situated, in the sample, at a depth from the surface, the depth being greater than the previously determined threshold depth of the sample;
- determining an optical scattering property of the sample;
- determining a correction term, as a function of the determined optical scattering property;
- determining a resulting correction function taking into account the said depth-wise Raman spectrum and the correction term;
- illuminating a surface of the sample by a second light beam, produced by a laser light source, the laser light source being coupled to a first optical system, focusing the second light beam in the first object focal plane of the first optical system, the first object focal plane being situated, in the sample, at a measuring depth z from the surface of the sample, the measuring depth being lower than threshold depth;
- measuring, with the Raman spectrophotometer, a second optical signal backscattered by the sample in response to the second light beam, the Raman spectrophotometer producing a second measured signal representative of the second optical signal at the measuring depth, thereby forming a Raman spectrum at the measuring depth, a spatial filter being interposed between the first optical system and the Raman spectrophotometer, the spatial filter comprising a window which transmits the said second optical signal towards the Raman spectrophotometer, the window being disposed in a conjugate focal plane of the object focal plane of the first optical system; and
- applying the correction function to the Raman spectrum at the measuring depth to generate a corrected Raman spectrum at the measuring depth.

21. The method according to claim 20, wherein the optical scattering property is a reduced scattering coefficient.

22. The method according to claim 20, wherein the correction function comprises:
- multiplying the Raman spectrum at the measuring depth by an exponential function, the exponential function depending on the correction term and on the measuring depth; and
- adding the depth-wise Raman spectrum to the product of the Raman spectrum at the measuring depth by the exponential function.

23. The method for correcting an optical signal produced according to claim 20, wherein the Raman spectrum at the measuring depth is corrected such that:

$$SP_{corr\text{-}z} = F_{corr}(SP_z) = [SP_z - SP_{depth}]e^{\beta(\mu_s') \times z} + SP_{depth}$$

wherein:
$SP_z$ is the spectrum measured at the measuring depth z;
$SP_{depth}$ is the depth-wise spectrum;
$\beta(\mu_s')$ is the correction term as a function on the optical scattering property; and
$F_{corr}$ is the correction function.

* * * * *